United States Patent
Bergkvist

(12) 
(10) Patent No.: US 6,234,170 B1
(45) Date of Patent: May 22, 2001

(54) GAS PRESSURE GENERATOR

(75) Inventor: Rune Bergkvist, Vaxholm (SE)

(73) Assignee: Siemens Elema AB, Solna (SE)

( * ) Notice: Subject to any disclaimer, the term of this patent is extended or adjusted under 35 U.S.C. 154(b) by 0 days.

(21) Appl. No.: 09/192,376

(22) Filed: Nov. 16, 1998

(30) Foreign Application Priority Data

Nov. 20, 1997 (SE) .................................................. 9704300

(51) Int. Cl.$^7$ ...................................................... A62B 7/00
(52) U.S. Cl. ................................ 128/205.18; 128/204.18
(58) Field of Search ........... 128/203.12, 205.13–205.16, 128/205.18, 204.18

(56) References Cited

U.S. PATENT DOCUMENTS

| | | | |
|---|---|---|---|
| 3,336,920 | * 8/1967 | Thomas | 128/205.18 |
| 3,530,856 | * 9/1970 | Bird et al. | 128/204.18 |
| 3,824,902 | 7/1974 | Olsson . | |
| 3,918,447 | 11/1975 | Inkster et al. . | |
| 4,010,761 | 3/1977 | Tipple . | |
| 4,836,198 | * 6/1989 | Gates | 128/205.18 |
| 5,484,270 | * 1/1996 | Adahan | 417/415 |

FOREIGN PATENT DOCUMENTS

| | | |
|---|---|---|
| 0 112 979 | 7/1984 | (EP) . |
| 0 283 141 | 9/1988 | (EP) . |
| 0 744 184 | 11/1996 | (EP) . |
| 2 054 387 | 2/1981 | (GB) . |

* cited by examiner

*Primary Examiner*—Glenn K. Dawson
(74) *Attorney, Agent, or Firm*—Schiff Hardin & Waite

(57) ABSTRACT

A gas pressure generator for a ventilator includes a variable volume container provided with an inlet connectable to a fresh gas supply and an outlet connectable to a respiration circuit of the ventilator and a driving fluid-actuated piston having a shaft with a piston head for transmitting the force to the variable volume container at one end and an opposite end, at which the force is generated, being moveable in a driving fluid chamber so to reduce the volume of the container to maintain a substantially constant output pressure of contained fresh gas. The driving fluid is maintained at a substantially constant pressure with the piston shaft and the chamber relatively dimensioned such that the percentage volume change within the chamber as the shaft moves therein is no greater than an allowable percentage variation in the output pressure of the fresh gas.

5 Claims, 1 Drawing Sheet

GAS PRESSURE GENERATOR

BACKGROUND OF THE INVENTION

1. Field of the Invention

The present invention relates to a gas pressure generator and in particular to a gas pressure generator of the type used to generate a substantially constant pressure of gas in a ventilator, especially fresh gas in an anesthesia ventilator.

2. Description of the Prior Art

Anesthesia ventilators are well known and generally contain a so-called "closed" or "partially closed" respiratory circuit, dependent on whether all or some of the exhaled respiratory gases are reused. These circuits reduce the consumption of fresh gas, for example respiratory air enriched with oxygen or anesthetic gas. In order to compensate for gas losses during a breathing cycle, a supply of fresh gas is provided for introduction into the respiratory circuit. The constituents of the fresh gas are often supplied from a high pressure source, such as a gas bottle or a hospital's centralized high pressure system, and its pressure must be reduced to around 100 cm $H_2O$ before being supplied to a patient.

It is also desirable that the fresh gas supply to the respiratory circuit be maintained at a substantially constant over-pressure, not least because the amount of fresh gas introduced can be more easily monitored if it is delivered at a substantially constant pressure. In order to obtain such a substantially constant pressure fresh gas source, it is usual to provide a source of fresh gas connectable to a gas pressure generator having a variable volume container with an output that is connectable to the respiratory circuit. The volume of the container is variable in a manner so that the input pressure of fresh gas can be reduced to a usable level and fresh gas at a substantially constant pressure can be supplied as an output.

Although referred to as a "constant" pressure source in reality the output pressure may be allowed to vary within limits (typically 10%–20% of the desired pressure) dependent on the circumstances of intended use in a manner known to those skilled in the art.

One known variable volume container is described in U.S. Pat. No. 3,824,902 and includes an expansion bellows made of soft plastic material attached between two rigid plates. One plate is spatially fixed and the other is operably connected to a shaft which, when rotated, collapses the container by means of springs. Through suitable choices of spring and spring attachment points the container can be made to collapse so that over a certain range of volumes the force exerted on the container is constant, thereby producing a constant pressure fresh gas output. Such a container, however, is mechanically complex which results in relatively high construction costs and likelihood of malfunction during use.

A further variable volume container is described in European Application 0 744 184 which also includes a collapsible bellows arrangement. This bellows is formed, at least in part, of an elastic material. Through careful choice of material and constructional configuration the bellows is made to produce, over a limited range of volume change, a constant pressure on the fresh gas contained in it as its volume reduces. Although a great simplification over the aforementioned container, a problem still remains that, as with the previously described bellows, the constant pressure gas can only be generated over a limited range of volume changes, which range tends to be removed from the zero volume condition.

This means that the container usually has a relatively large "dead volume" of fresh gas in it which is not removed during the breathing cycle of a patient. This may cause problems when a change in the constituents of the fresh gas is needed during an operation because a relatively large, often expensive, volume of gas has to be flushed out of the container. This is time consuming and fresh gas cannot be supplied, or is supplied but with an unknown constituency, to the patient during this time.

SUMMARY OF THE INVENTION

It is an object of the present to provide a gas pressure generator which supplies a gas at a constant (as defined above) pressure wherein the above-described problems associated with conventional generators of this type are avoided.

This object is achieved in accordance with the principles of the present invention in a gas pressure generator for a ventilator having a variable volume container provided with an inlet connected to a fresh gas supply, and an outlet connectable to a respiration circuit of the ventilator, a driving fluid-actuated piston with a shaft and a piston head for transmitting a force to the variable volume container at one end, and having an opposite end, at which the force is generated, which is movable in a chamber containing the driving fluid, the piston being movable so as to reduce the volume of the container to maintain a substantially constant output pressure of fresh gas contained therein, wherein the driving fluid container contains driving fluid at a substantially constant pressure, and wherein the piston shaft and the chamber are dimensioned relative to each other so that a percentage volume change within the chamber as the shaft moves therein is no larger than air allowable percentage variation in the output pressure of the fresh gas.

By a suitable choice of dimensions of the piston shaft and driving fluid (hydraulic or pneumatic) chamber, a piston can be provided in which the driving fluid pressure is maintained substantially constant throughout the stroke length of the piston which tends to collapse the variable volume container. In this manner a substantially constant output pressure of contained gas can be provided by a gas pressure generator which is relatively mechanically simple and reliable. Such a generator can be readily constructed so as to be capable of operating to provide fresh gas which is supplied at a substantially constant pressure over the entire volume of the variable volume container.

Advantageously the piston shaft is movable in a driving fluid chamber dimensioned so the percentage change in its internal volume is no greater than the allowable percentage change in fresh gas output pressure. This provides for a simple construction of the driving fluid section of the gas generator, which may even be formed as a sealed unit.

For ease of construction the gas generator may be formed from a single piston housing which includes compartments to contain the driving fluid chamber and the variable volume container.

DESCRIPTION OF THE PREFERRED EMBODIMENTS

Figure 1:
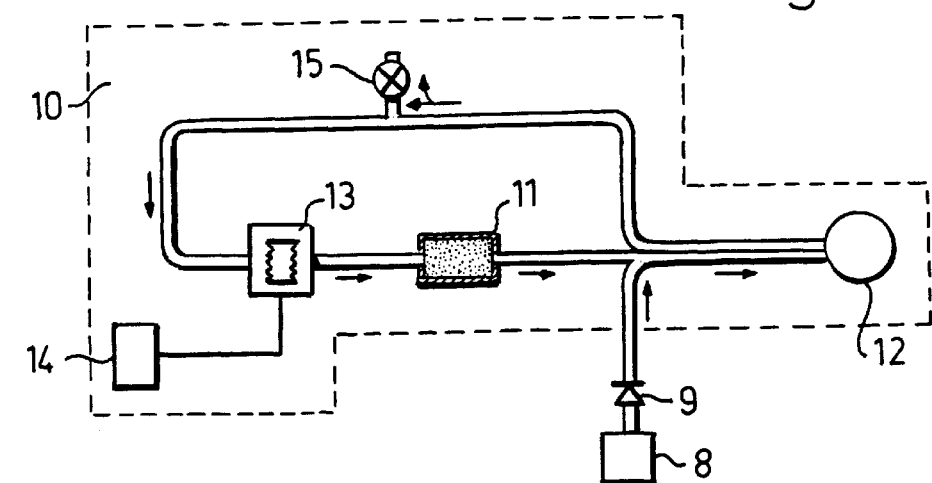
FIG. 1 shows an embodiment of a gas pressure generator constructed in accordance with the invention, in connection with an anesthesia/ventilator system.

The anesthesia ventilator system shown in FIG. 1 includes a gas pressure generator 1 according to the present invention, but is otherwise of a generally known construction.

A gas mixer 2 can be supplied with gases such as nitrous oxide via the connection 3, oxygen via the connection 4 and air via the connection 5. During anesthesia, a patient is usually only supplied a mixture of nitrous oxide and oxygen, together with the anesthetizing agent which is introduced via a vaporizer 6. To awaken the patient a mixture of air and oxygen may be supplied to the patient from the mixer 2.

Breathing gas can pass from the vaporizer 6 into the gas pressure generator 1 via a valve 7. Fresh breathing gas can then be conducted from the generator 1 through a flow meter 8 and a one way valve 9 to the inspiration side of a ventilator system 10. The valve 9 controls the flow of the fresh gas to the ventilator system 10 dependent on the flow measured by the flow meter 8.

The ventilator system 10 has a closed respiratory 5 circuit with breathing gas circulating in the direction of the arrows. Pulses of breathing gas, for example corresponding to a desired breathing pattern, are provided to a patient via a carbon dioxide scrubber 11 and a face mask 12. Exhaled gas passes via the face mask 12 to a bellows 13 which is compressed to provide the pulses of breathing gas in dependence on an electrical signal from a controller 14. A pressure release valve 15 is also provided in the exhalation side of the respiratory circuit, for safety.

In order to obtain as precise a flow value as possible, and therefore a precise anesthetic dose to the patient, the pressure of the fresh gas in the gas pressure generator 1 is controlled so as to be constant. This is achieved using the below described gas pressure generator 1 according to the present invention.

The gas pressure generator 1 includes piston housing 29 which includes compartments 16,17 to house the variable volume container 30 and driving fluid chamber 17, respectively. The compartments 16,17 are separated by a rigid wall 18. A piston shaft 19 passes from the chamber 17 to the container 16 through a fluid-tight seal 20 in the wall 18 for reciprocal movement in the two compartments 16,17. A piston head 21 is attached to one end of the shaft 19 and constitutes a movable wall of the variable volume container 30 which is formed by the region of the container 16 between the piston head 21 and an end wall of the piston housing 29. An air vent 22 is disposed in a wall of the housing 29 and is positioned to always remain in a region between the piston head 21 and the wall 18. The vent 22 then operates to maintain that region at atmospheric pressure as the piston formed by the piston shaft 19 an the piston head 21 reciprocates.

Driving fluid is contained within the driving fluid chamber 17 and is pressurized to exert a force on the end of the shaft 19, lying within the chamber 17. This force is then transmitted through the shaft 19 to the piston head 21 to exert a pressure on the fresh gas contained in the variable volume container 30. When the pressure of the supplied fresh gas exceeds this pressure exerted by the piston, the head 21 is moved toward the rigid wall 18. This increases the variable volume of the container 30 and so reduces the pressure of the supplied gas contained therein until the forces acting on either side of the piston head 21 reach equilibrium. As a consequence of the head 21 moving, the end of the shaft 19 moves further into the chamber 17, reducing its volume and so proportionally increasing the pressure of the fluid contained in it.

By a suitable choice of shaft and chamber dimensions the fluid may provide, via the piston head 21, a pressure on the fresh gas within the container 30 which is substantially constant for all of the piston stroke.

The driving fluid chamber 17 shown in FIG. 1 is a sealed unit and so provides an essentially fixed operating pressure. An alternative embodiment is shown by the broken lines in FIG. 1. The driving fluid chamber 17 may be connected to a source of pressurized driving fluid 23, such as the pressurized air supply of a hospital, via a controllable pressure regulator 24. This enables the pressure of the fluid within the chamber 17 to be varied so as to vary the pressure of the constant pressure fresh gas supply.

EXAMPLE

The dimensions of the gas generator 1 can be selected by a person skilled in the art using equations common to the art for any given desired output pressure and pressure of driving fluid.

Consider, for example, a gas pressure generator 1 by which it is desired to generate a fresh gas output at a constant over-pressure of 0.1 bar ($P_1$), using a driving fluid pressurized at an over-pressure of 1 bar ($P_2$) when the volume of the container 16 is at a minimum.

Using a typical cross-sectional area for the gas generator 1 of 38 cm² ($A_1$) then the force ($F_1$) exerted by the piston head 21 (being of substantially the same cross section as the gas generator 1) is given by $$F_1 = P_1 \times A_1 \times g \tag{1}$$

where g=gravitational constant
Using equation (1) $F_1 \approx 0.1$ kgcm$^{-2}$×38 cm²×9.81≈37 N
The force ($F_2$) exerted by the driving fluid on the shaft 19 should equal to $F_1$ thus by analogy with equation (1)

$$F_2 = F_1 = P_2 \times A_2 \times g \tag{2}$$

where $A_2$ is the required shaft area
This gives $A_2 \approx 37$ N/(1 kgcm$^{-2}$×9.81)≈3.8 cm²

The volume of the chamber 17 for given operating conditions i.e., with a knowledge of fresh gas supply pressure and permitted percentage variation in output pressure $P_2$ the required change in volume of the variable volume container (and hence length (1) the shaft 19 consequently moves into the chamber 17) can be calculated using the ideal gas equation:

$$P \times V = R \times T \tag{3}$$

| where | P | is the gas pressure, |
|---|---|---|
| | V | is the volume occupied by the gas |
| | R | is the universal gas constant |
| | T | is the temperature of the gas |

Assuming that a 10% increase in output pressure $P_1$ is acceptable (and therefore a 10% variation in $P_2$) over the length (1) the piston moves then from equation (3) a 10% variation in volume of the chamber 17 is acceptable.

Figure 2:
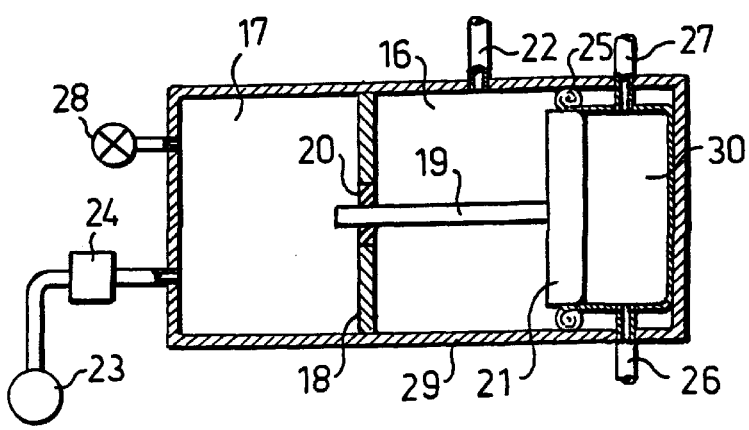
FIG. 2 shows an alternative construction of the gas pressure generator of the present invention, substitutable for that of FIG. 1 in the anesthesia system.

Considering now FIG. 2, a gas pressure generator 1 is shown in which components similar to the generator of FIG. 1 are given the same reference numeral. The gas pressure generator 1 again includes a piston housing 29 having two compartments 16, 17 separated by a rigid wall 18. A piston head 21 is mounted at the end of a shaft 19 for reciprocal movement in the compartment 16 which contains a variable volume container 30 constructed from a "rolling" bellows 25 arrangement. This arrangement includes a foldable (rollable) fabric bellows 25 having one end secured to the end wall of the compartment 16 and the other to the piston head 21 so that as the piston head moves towards the rigid wall 18 the fabric unfolds (unrolls) and the internal volume of the variable volume container 30 increases. A gas inlet 26 and an outlet 27 are provided to connect the internal volume of the bellows 25 to a fresh gas supply. By using a gas generator which includes a bellows arrangement as the variable volume container 30, the air vent 22 can be placed anywhere in the wall of the container 16 (indeed the container 16 may even be removed if desired) so that the length of the container 16 need be no greater than the maximum piston stroke length.

The chamber 17 is provided with a pressure control system 23,24,28 which acts to maintain the driving fluid in the chamber 17 constant as the shaft moves within it. Pressurized fluid from a supply 23 passes through a variable pressure regulator 24 to maintain a constant pressure fluid input to the chamber 17. A pressure release valve 28 is also included in the chamber 17 to vent the fluid if its pressure rises above the desired constant pressure (i.e. as the movement of the shaft 19 reduces the volume of the chamber 17).

Although modifications and changes may be suggested by those skilled in the art, it is the intention of the inventor to embody within the patent warranted hereon all changes and modifications as reasonably and properly come within the scope of his contribution to the art.

I claim as my invention:

1. A gas pressure generator for a ventilator, comprising:
   a variable volume container having an inlet connectable to a fresh gas supply, and an outlet connectable to a respiration circuit of a ventilator;
   a driving fluid chamber containing driving fluid at a substantially constant pressure;
   a piston, actuated by said driving fluid, having a shaft with a piston head disposed at a first end of said shaft for transmitting a force to said variable volume container, and said shaft having an opposite second, free end disposed in and movable in said driving fluid chamber, said driving fluid acting on said second, free end of said shaft to transmit a force to said piston head, said force causing said piston head to move within said variable volume container to reduce a volume of said variable volume container to maintain a substantially constant output pressure of fresh gas contained in and expelled from said variable volume container; and
   said piston shaft and said driving fluid chamber having relative dimensions for causing a percentage volume change within said driving fluid chamber as said shaft moves therein to be no greater than a predetermined variation in said output pressure of said fresh gas.

2. A gas generator as claimed in claim 1 wherein said driving fluid chamber includes pressure regulation means for maintaining a pressure of the driving fluid contained within said driving fluid chamber at a constant value over operating volumes of said variable volume container.

3. A gas generator as claimed in claim 1 comprising a piston housing which is compartmentalized for housing said variable volume container and said driving fluid chamber.

4. A gas generator as claimed in claim 3 wherein said variable volume container comprises a rolling bellows having a lower surface attached to said piston housing and having an upper surface attached to said piston head to roll and unroll as said piston head reciprocates.

5. An anesthesia ventilator comprising:
   a fresh gas delivery system including a mixer for combining a plurality of constituent gases to produce mixed gases and means for introducing an anesthetic into the mixed gases to form a fresh anesthetic gas supply, said fresh gas delivery system having an output;
   a gas pressure generator having an inlet connected to said outlet of said fresh gas delivery system;
   a respiratory circuit for supplying a patient with pulses of breathing gas, said respiratory circuit having an input connected to an output of said gas pressure generator;
   said gas pressure generator comprising:
   a variable volume container having an inlet connectable to a fresh gas supply, and an outlet connectable to a respiration circuit of a ventilator;
   a driving fluid chamber containing driving fluid at a substantially constant pressure;
   a piston, actuated by said driving fluid, having a shaft with a piston head disposed at a first end of said shaft for transmitting a force to said variable volume container, and said shaft having an opposite second, free end disposed in and movable in said driving fluid chamber, said driving fluid acting on said second, free end of said shaft to transmit a force to said piston head, said force causing said piston head to move within said variable volume container to reduce a volume of said variable volume container to maintain a substantially constant output pressure of fresh gas contained in and expelled from said variable volume container; and
   said piston shaft and said driving fluid chamber having relative dimensions for causing a percentage volume change within said driving fluid chamber as said shaft moves therein to be no greater than a predetermined variation in said output pressure of said fresh gas.

* * * * *